(12) United States Patent
Sayet et al.

(10) Patent No.: US 7,037,276 B2
(45) Date of Patent: May 2, 2006

(54) BIOPSY DEVICE

(75) Inventors: Peter H. Sayet, Fort Lauderdale, FL (US); Lloyd A. Sutherland, Boca Raton, FL (US); Michael Wolfe, Newton, MA (US)

(73) Assignee: Precision Medical Devices, Inc., Fort Lauderdale, FL (US)

( * ) Notice: Subject to any disclaimer, the term of this patent is extended or adjusted under 35 U.S.C. 154(b) by 406 days.

(21) Appl. No.: 10/187,564

(22) Filed: Jul. 2, 2002

(65) Prior Publication Data

US 2004/0006284 A1    Jan. 8, 2004

(51) Int. Cl.
*A61B 10/00* (2006.01)

(52) U.S. Cl. .................. 600/564; 606/106; 606/170

(58) Field of Classification Search ................ 600/562, 600/564, 565, 566, 567, 570; 606/106, 108, 606/110, 167, 170, 185, 205–212
See application file for complete search history.

(56) References Cited

U.S. PATENT DOCUMENTS

| 4,467,802 A | 8/1984 | Maslanka |
| 4,655,219 A | 4/1987 | Petruzzi |
| 4,781,191 A | 11/1988 | Thompson |
| 4,994,079 A | 2/1991 | Genese et al. |
| 5,269,780 A | 12/1993 | Roos |
| 5,271,385 A | 12/1993 | Bailey |
| 5,306,284 A * | 4/1994 | Agee et al. .................. 606/170 |
| 5,320,627 A | 6/1994 | Sorensen et al. |
| 5,336,228 A | 8/1994 | Cholhan |
| 5,474,057 A | 12/1995 | Makower et al. |
| 5,520,704 A | 5/1996 | Castro et al. |
| 5,586,990 A * | 12/1996 | Hahnen et al. ............. 606/170 |
| 5,769,865 A * | 6/1998 | Kermode et al. ........... 606/167 |
| 5,776,075 A | 7/1998 | Palmer |
| 5,843,000 A * | 12/1998 | Nishioka et al. ............ 600/566 |
| 5,928,264 A | 7/1999 | Sugarbaker et al. |
| 5,971,940 A | 10/1999 | Baker et al. |
| 5,980,534 A | 11/1999 | Gimpelson |
| 6,027,518 A | 2/2000 | Gaber |
| 6,447,525 B1 * | 9/2002 | Follmer et al. ............. 606/159 |
| 2002/0177874 A1 * | 11/2002 | Nicholas et al. ............ 606/206 |
| 2003/0158498 A1 * | 8/2003 | Bakry ........................ 600/562 |
| 2003/0176880 A1 * | 9/2003 | Long et al. ................. 606/167 |

\* cited by examiner

*Primary Examiner*—Charles Marmor
(74) *Attorney, Agent, or Firm*—Akerman Senterfitt

(57) ABSTRACT

A biopsy device includes a housing and at least one biopsy mechanism moveably connected to the housing. The biopsy can be provided on a biopsy arm. An actuator moves the biopsy arm and operates the biopsy mechanism. The biopsy arms with the biopsy mechanisms are preferably removable from the housing, such that the housing can be used again for subsequent biopsy procedures.

5 Claims, 7 Drawing Sheets

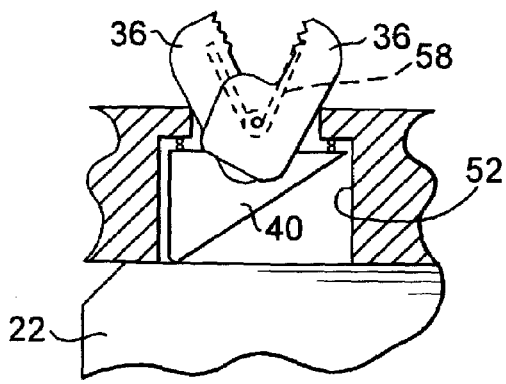
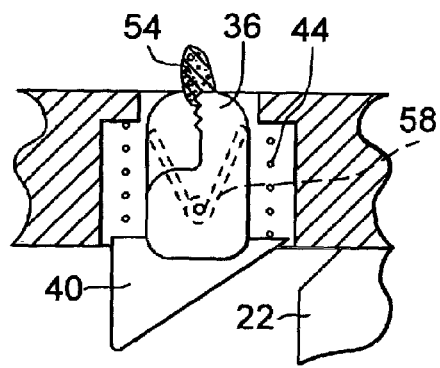
FIG. 6(a)  FIG. 6(b)
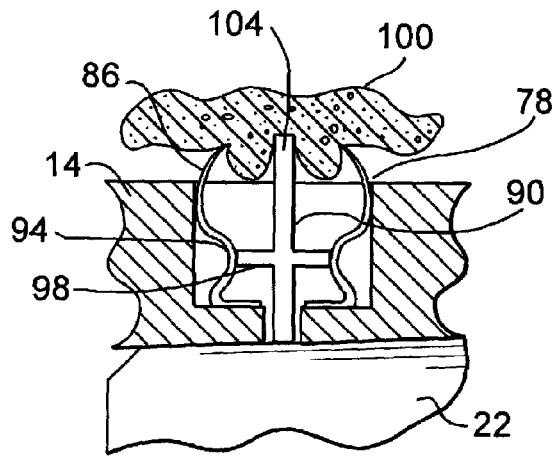
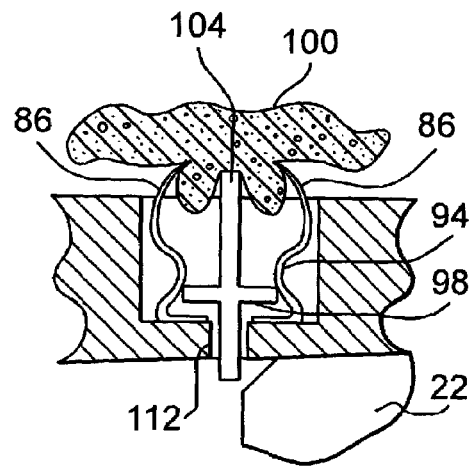
FIG. 8(a)  FIG. 8(b)
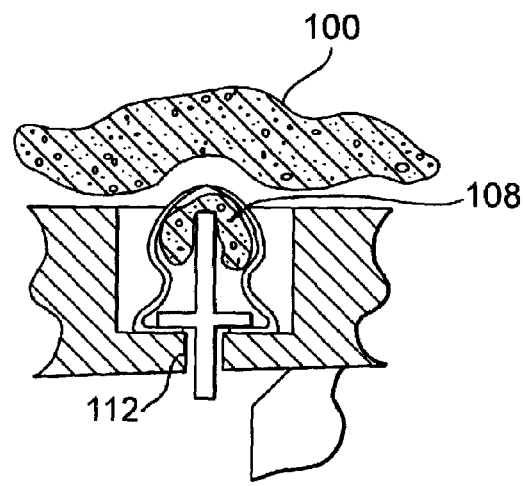
FIG. 8(c)

BIOPSY DEVICE

FIELD OF THE INVENTION

This invention relates generally to medical instrumentation, and more particularly to biopsy devices.

BACKGROUND OF THE INVENTION

Biopsy devices are used to obtain tissue samples, usually for purposes of performing testing on these samples. In order to obtain a biopsy sample, the biopsy device must be inserted into the body to reach the tissue for which the biopsy is to be taken. The device must be positioned next to the tissue, the sample taken, and the device removed. Some biopsy protocols require multiple samples to be taken. In the case of a body canal, samples from different positions on the circumference of the canal are sometimes required for each axial position along the canal length. This can require multiple devices if sterility and sample integrity are to be maintained, or multiple procedures if more than one biopsy site is required to be sampled.

It is difficult to maintain the stability and position of a biopsy device upon insertion into the body. Biopsy procedures usually involve small incisions such that manipulation of the device at the point of the biopsy is not directly possible. It is possible for the biopsy sample to become dislodged from the biopsy device during removal of the device from the body. Secure retention of the sample is necessary to avoid repeating the process.

SUMMARY OF THE INVENTION

A biopsy device includes a housing and at least one biopsy mechanism connected to the housing. The biopsy mechanism can be provided on a biopsy arm that is connected to the housing. An actuator is provided for moving the biopsy arm and operating the biopsy mechanism.

The biopsy mechanism can comprise jaws adapted to engage and remove a biopsy sample. The jaws can be biased to an open position. The actuator can contact the jaws, a cam, or other structure connected to the jaws, such that movement of the actuator opens the jaws.

The actuator can comprise a moveable plunger. The housing can include an open interior and the plunger can be provided in the open interior. Movement of the plunger contacts the cam or other structure to operate the biopsy mechanism. Movement of the plunger can also move the biopsy arm radially outward relative to the housing. This movement will position the biopsy mechanism against the tissue to be sampled. Thus, a single stroke of the actuator can move the biopsy mechanism into position and operate the biopsy mechanism to take the sample. Gripping structure can be provided on the housing and the plunger so as to facilitate relative movement of the plunger within the housing.

Movement of the actuator in a first direction can force the biopsy arm radially outward and causes the biopsy mechanism to open. Movement of the actuator in a second direction causes the biopsy arm to move radially inward and the biopsy mechanism to close. Alternatively, the actuator can be constructed such that movement in one direction will in one position open the biopsy mechanism, and movement to another position, but in the same direction, will close the biopsy mechanism.

The biopsy mechanism can be biased to an open position or a closed position. A cam can be operatively connected to the biopsy mechanism. Contact between the actuator and the cam causes the biopsy mechanism to open or close against the biasing. The biopsy mechanism should be in the closed position prior to the biopsy arm moving radially inward such that the sample will be securely retained.

In a preferred embodiment, a plurality of biopsy arms are provided. A plurality of radially disposed biopsy arms can be spaced about an end of the housing. A first end of each arm can be connected to the housing. Each biopsy arm has a biopsy mechanism such that movement of the actuator actuates each of the biopsy arms and the respective biopsy mechanism. The biopsy mechanism can be provided at or near an opposing end of the biopsy arm. Two or more arms are preferred. Four or more radially disposed arms permit sampling about the circumference of a canal or orifice, such as the esophagus.

The biopsy arms can be provided on a head that is removably attached to the housing. In this manner, the head can be removed after the biopsy is performed and the housing and related actuator mechanism can be refitted with another head for taking another sample. The removed head with the biopsy samples is then processed to remove the samples for laboratory analysis.

A biopsy method includes the steps of providing a biopsy device with a housing and at least one biopsy mechanism connected to the housing. Structure is provided for moving the biopsy mechanism and actuating the biopsy mechanism. The biopsy mechanism can be provided on a biopsy arm that is connected to the housing. The device is inserted adjacent to tissue and the actuator is manipulated in order to move the biopsy mechanism into position and to operate the biopsy mechanism to obtain a sample.

BRIEF DESCRIPTION OF THE DRAWINGS

There are shown in the drawings embodiments which are presently preferred, it being understood however, that the invention is not limited to the precise arrangements and instrumentalities shown, wherein:

FIGS. 6(a)–(b) are enlarged cross sections of the biopsy mechanism of FIG. 5 as used during a biopsy procedure.

FIGS. 8(a)–(c) are cross sections illustrating a biopsy procedure utilizing an alternative biopsy mechanism according to the invention.

DETAILED DESCRIPTION OF THE PREFERRED EMBODIMENTS

Figure 1:
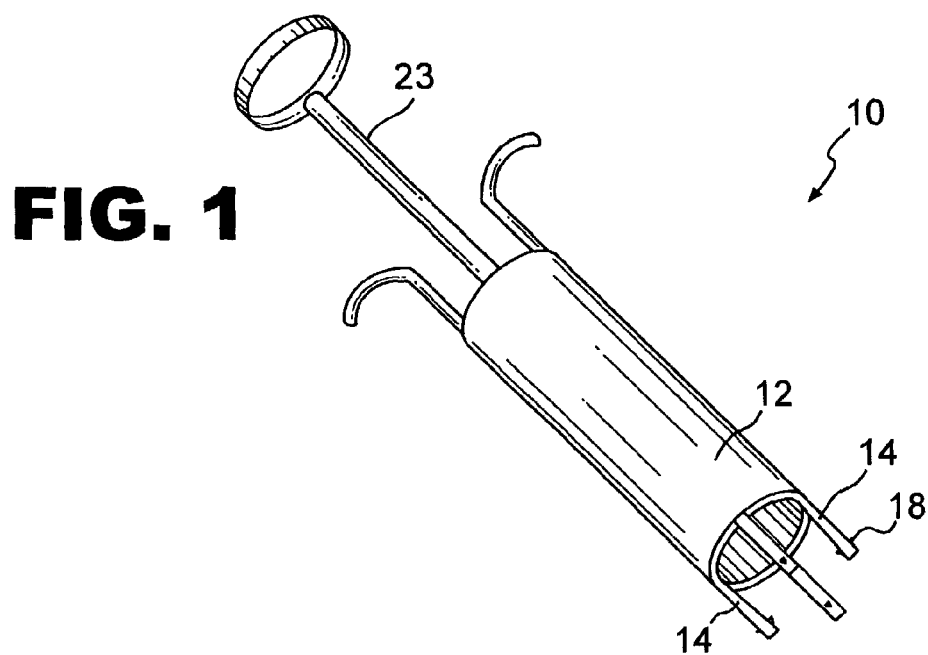
FIG. 1 is a perspective view of a biopsy device according to the invention.

A biopsy device 10 according to the invention is shown in FIG. 1. The biopsy device 10 includes a housing 12 and at least one biopsy mechanism 18. The housing 12 can be of any suitable construction. The biopsy mechanism 18 can be provided on a biopsy arm 14. Any number of biopsy arms 14 can be provided, however, at least two and preferably at least four biopsy arms 14 are preferred.

Figure 2:
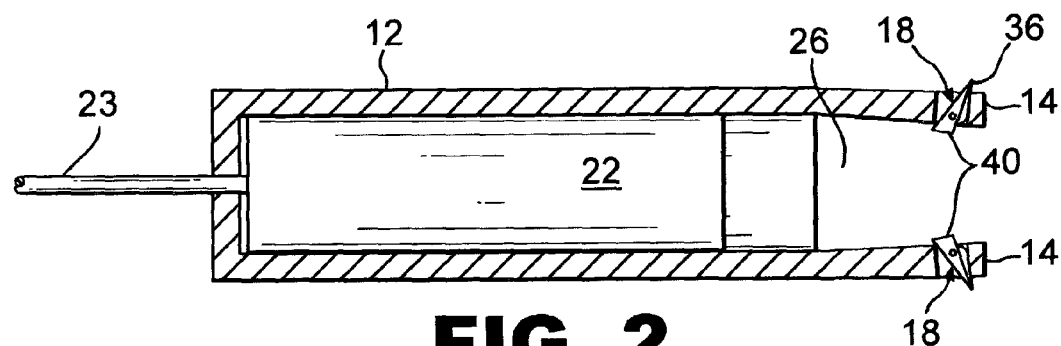
FIG. 2 is a cross section of a biopsy device according to the invention, and in a first mode of operation.
Figure 3:
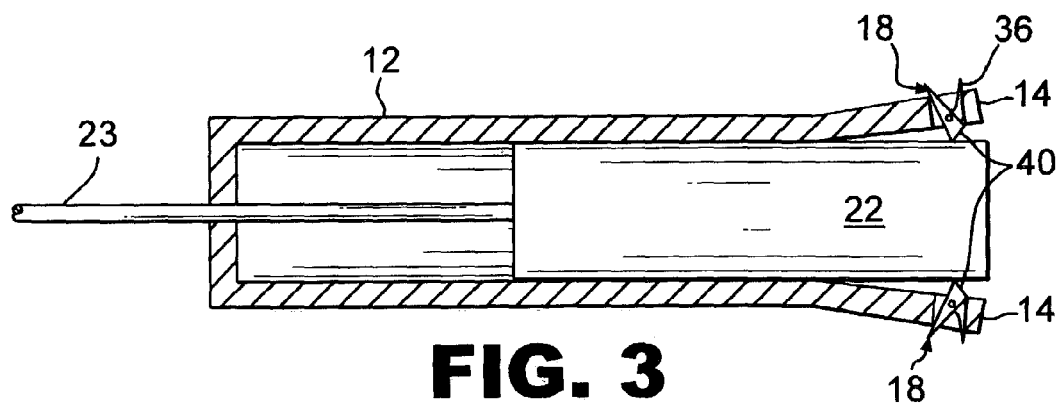
FIG. 3 is a cross section depicting a second mode of operation.

An actuator is provided for moving the biopsy mechanism outward relative to the housing 12 and operating the biopsy mechanism 18. The actuator can be a single mechanism or multiple mechanisms. Any suitable actuator mechanism(s) can be utilized. In one embodiment, the actuator comprises a plunger 22 which is moveable within an open interior 26 of the housing 12. Suitable structure such as handle 23 can be provided for manipulating the plunger 22. Movement of the actuator operates the biopsy mechanism 18 as shown in FIGS. 2–3. In one embodiment, the plunger 22 is operable to contact the biopsy mechanism 18 in such a manner as to operate the biopsy mechanism 18. A cam 40 can be associated with the biopsy mechanism 18. The movement of the plunger 22 contacts the cam 40 (FIG. 3) to operate the biopsy mechanism 18.

Figure 4A:
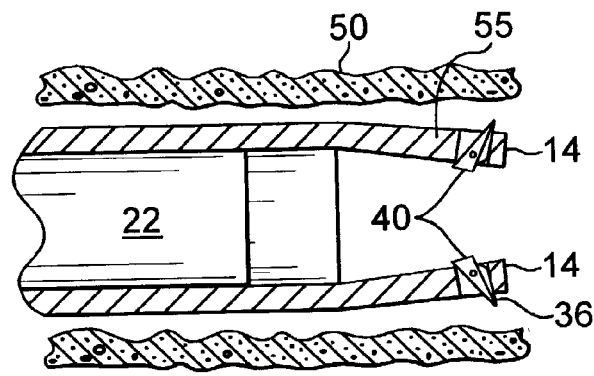
FIGS. 4(a)–(c) are cross sections depicting successive steps in a biopsy procedure according to the invention.
Figure 4B:
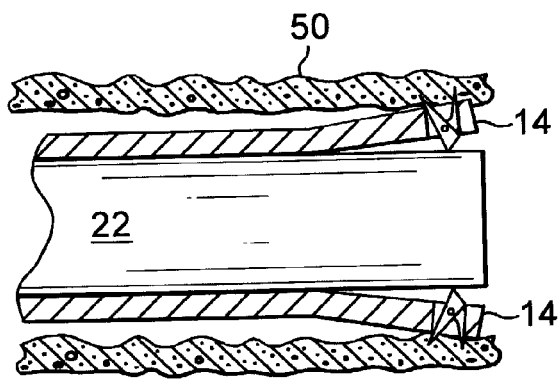
Figure 4C:
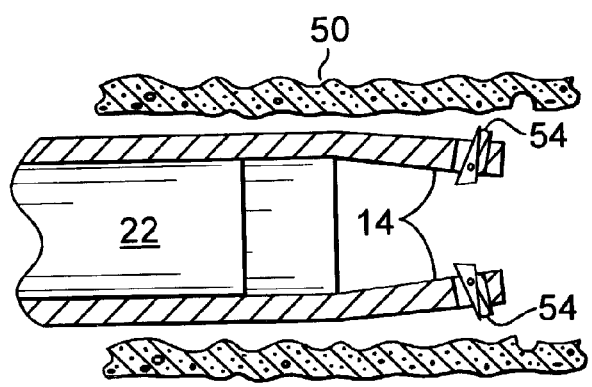
Figure 5A:
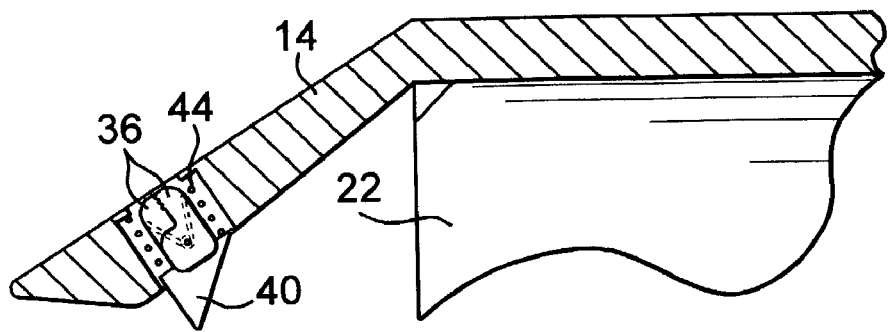
FIGS. 5(a)–(b) are cross sections depicting the operation of a biopsy mechanism according to the invention.
Figure 5B:
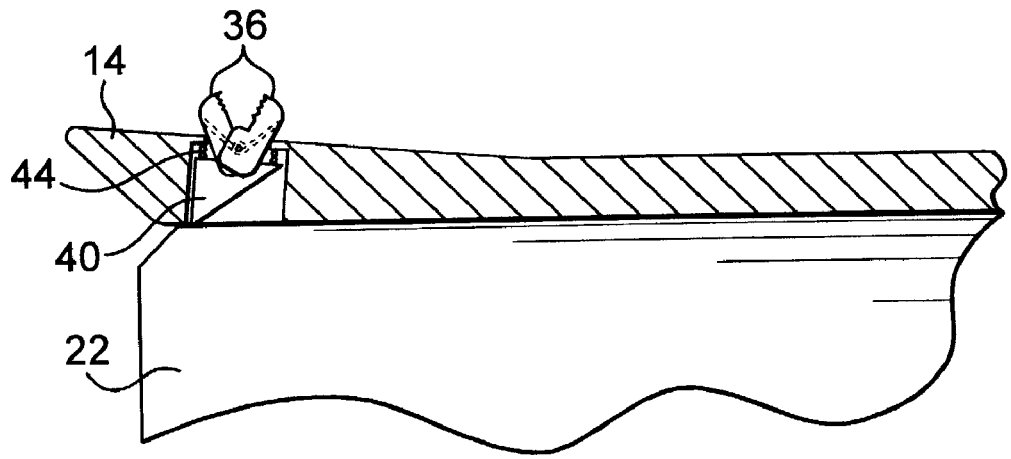

The biopsy mechanism 18 can be of any design that is suitable to remove a biopsy sample when actuated. The biopsy mechanism 18 is provided by suitable structure such that the biopsy mechanism is moved into position and operated to take the sample, preferably in a single action. In one design, the biopsy mechanism 18 comprises forceps 36. As shown in FIGS. 4–6, the forceps 36 are associated with suitable structure, such as cam 40, to operate the forceps 36. Biasing, such as spring 44, can be provided to bias the forceps 36 to a normally-closed position. Movement of the plunger 22 from a position within the housing 12 as shown in FIG. 5(a) to the position shown in FIG. 5(b) causes the plunger 22 to contact the cam 40. The cam 40 is moved within the cam seat 52 from the position shown in FIG. 5(a) to the position shown in FIG. 5(b) against the action of the spring 44. The forceps 36 are moved outward from the biopsy arm 14 and open through the operation of suitable structure such as spring 58 as shown in FIG. 6(a). The biopsy arms 14 can be provided with a substantially wedge-shaped portion 55 as shown in FIG. 4(a). Movement of the plunger 22 causes the plunger 22 to contact the wedge portion 55 to cause the biopsy arms 14 to move outward as shown in FIGS. 4(a)–(c). Retraction of the plunger 22 causes the return of the forceps 36 from the open position shown in FIG. 4(b) to the closed position and inward movement of the biopsy arms 14, as shown in FIG. 4(c). Other structure for moving the biopsy arms 14 and biopsy mechanisms 18 outward and inward are alternatively possible.

In operation, the biopsy device 10 is positioned in a portion of the body such as canal 50, although it will be appreciated that the biopsy device 10 of the invention can be utilized to biopsy tissues throughout the body. The plunger 22 is initially in the retracted position. When the biopsy device 10 has been properly positioned, movement of the plunger 22 causes the plunger 22 to contact wedge portions 55 of the biopsy arms 14 to move the biopsy arms 14 radially outward toward the walls of the canal 50 as shown in FIG. 4(b). The plunger 22 also contacts the cam 40 to cause the forceps 36 to move from the normally-closed position to the open position. Thus, the biopsy mechanisms 18 are centered and forced toward the walls of the canal 50 and are opened for taking a sample. The biopsy device 10 of the invention permits, in one action, the outward movement of the biopsy arms 14 and the operation of the biopsy mechanism 18. Upon retraction of the plunger 22, the plunger 22 is removed from contact with the cam 40 which causes the forceps 36 to close under the action of the biasing spring 44. A tissue sample 54 is removed by the forceps 36. Also, retraction of the plunger 22 permits the biopsy arms 14 to move radially inward and away from the walls of the canal 50, as shown in FIG. 4(c). This will permit retraction of the biopsy device 10 whereupon the biopsy device 10 can be removed and the sample 54 can be obtained. The retraction of the plunger 22 closes the forceps 36 before the retraction of the plunger 22 causes significant inward movement of the biopsy arms 14, such that the sample 54 is removed before the biopsy mechanism 18 is moved away from the tissue.

Figure 7A:
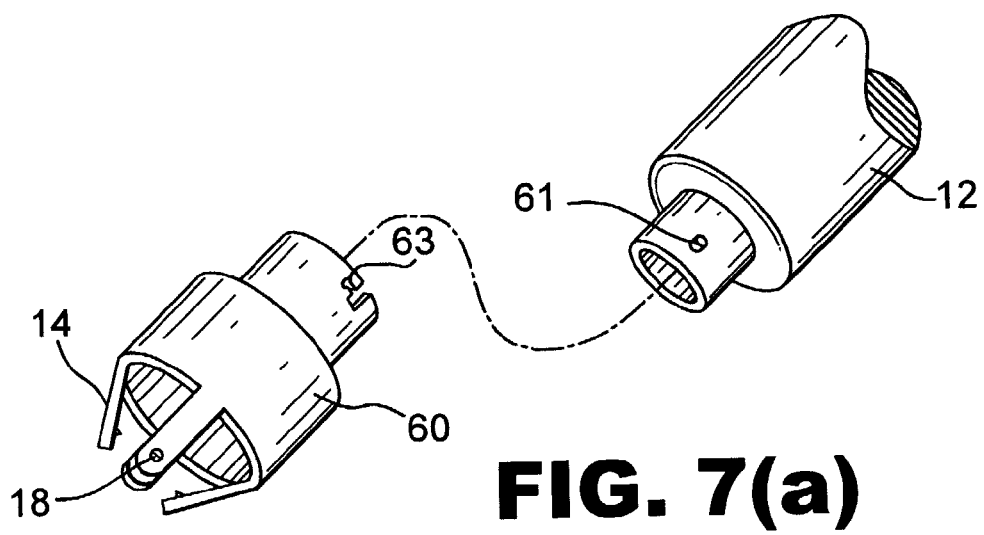
FIGS. 7(a)–(b) are exploded perspective views illustrating an alternative embodiment of the invention.
Figure 7B:
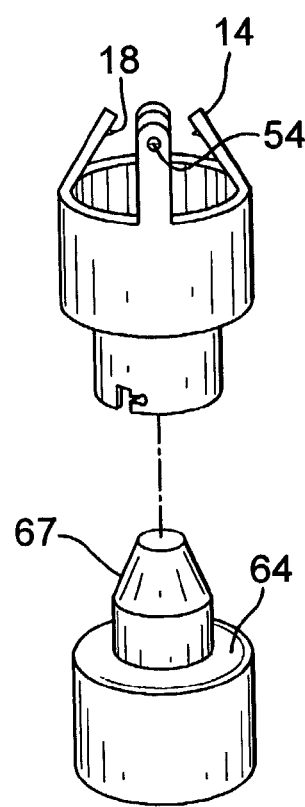

In some biopsy protocols, it is necessary to repeatedly biopsy in incremental lengths. For example, in a biopsy for Barretts Metaplasia (cancer of the esophagus), the protocol requires that a biopsy be taken every 5–20 mm. The repetition of the sampling can be tedious and time consuming. The biopsy device 10 according to the invention permits the sampling of the esophageal tissue about the circumference of the esophagus in a single action. Further, according to another embodiment of the invention, the removal of the biopsy sample 54 can be readily obtained. In this embodiment, shown in FIGS. 7(a)–(b), the biopsy arms 14 and biopsy mechanisms 18 are provided on a head 60. The head 60 is removably connected to the housing 12. The connection can be made by any suitable structure, such as the interlocking tongue 61 and groove 63 structure that is shown. Upon the taking of a biopsy sample 54, the biopsy device 10 is removed from the body and the head 60 is disconnected from the housing 12. The biopsy sample 54 can then be removed by manipulating the head 60 on a removal device 64. The removal device 64 can have a plunger 67 which is inserted into the head 60 to contact the biopsy mechanisms 18 to cause the mechanisms to open and release the samples 54. The head 60 can then be discarded or cleaned and sterilized for further use.

The operation of an alternative embodiment of a biopsy mechanism according to the invention is shown in FIGS. 8(a)–(c). The biopsy mechanism 78 is provided in a suitable seat in the biopsy arm 14. Spring arms 86 are held open by contact with a piston 90. Inward protruding portions 94 are contacted by a cross-piece 98 of the piston 90 to retain the spring arms 86 in the open position shown in FIG. 8(a). The biopsy arm 14 is then forced against the tissue 100, as by movement of the plunger 22 which wedges the biopsy arms 14 outward. Outward movement of the biopsy arms 14 causes end 104 of piston 90 to contact the tissue 100, which forces the crosspiece 98 of the piston 90 away from the inward protruding portions 94 of the spring arms 86, as shown in FIG. 8(b). The spring arms 86 then spring closed, and a sample 108 is removed from tissue 100. Retraction of the plunger 22 causes the piston 90 to retract through an opening 112, the spring arms 86 to close securely, and the sample 108 to be secured between the spring arms 86. This position is shown in FIG. 8(c). The device can then be removed from the body to retrieve and process the biopsy samples.

Figure 9A:
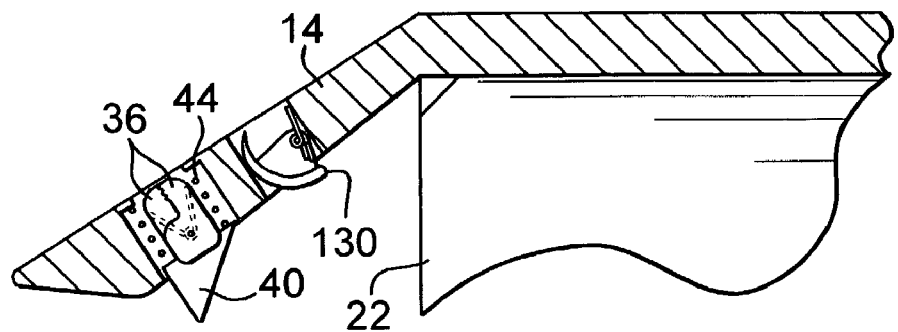
FIGS. 9(a)–(b) are cross sections illustrating the operation of an alternative embodiment.
Figure 9B:
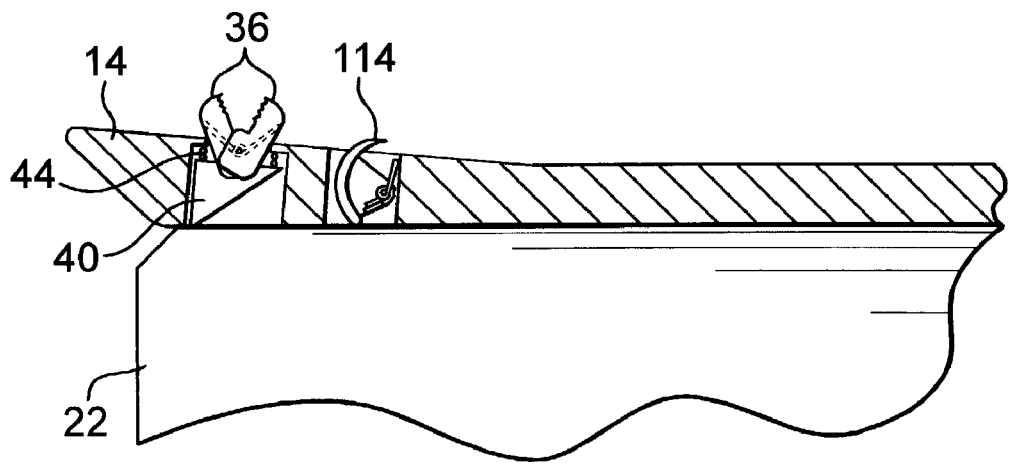
Figure 10:
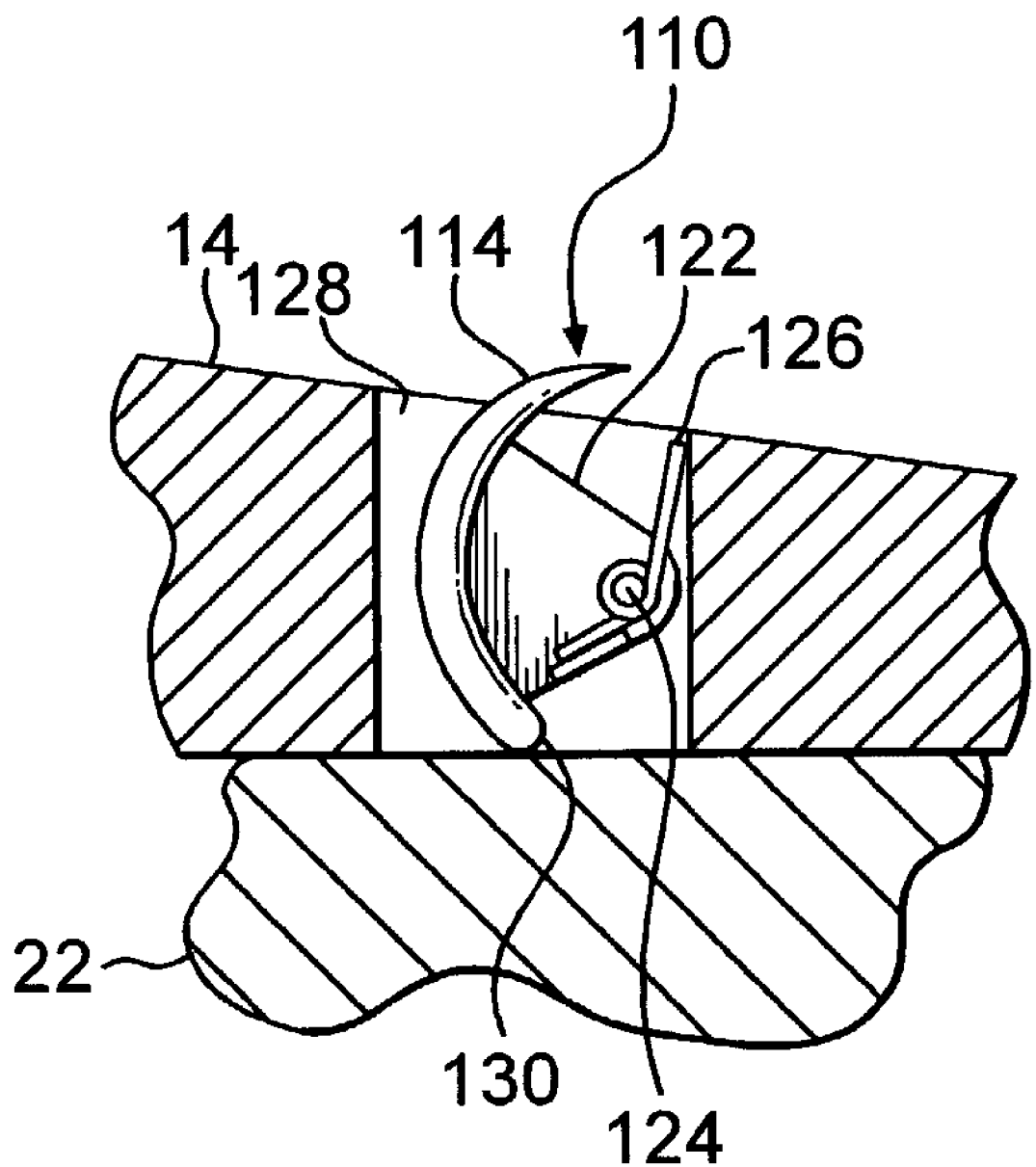
FIG. 10 is a cross section illustrating a gripping device of the alternative embodiment of FIG. 9.

There is shown in FIGS. 9–10 an alternative embodiment comprising a gripping device 110 for securing the biopsy arms 14 to the surrounding tissue so as to facilitate the taking of a sample. The gripping device 110 includes suitable structure for gripping the tissue such as a projection 114 having a sharp end. The projection 114 is movable in an opening 128. In one embodiment, the projection 114 is mounted on a carrier 122 which is pivotally mounted to biopsy arm 14 by pin 124. Suitable biasing such as spring 126 can bias the projection 114 to a retracted position. Movement of the plunger 22 contacts end 130 of projection 114 as the plunger moves from the retracted position shown in FIG. 9(a) to the extended position shown in FIG. 9(b). As the biopsy arm 14 is thereby moved outward, the projection 114 is extended and the sharp end enters the surrounding tissue to secure the biopsy arm 14 in position while the biopsy is taken. The biopsy mechanism can be as previously described including forceps 36, cam 40 and spring 44, or can be of an alternative construction. Upon retraction of the plunger 22, the forceps 36 will close prior to retraction of the projection 114 such that the biopsy sample will be removed before the surrounding tissue is released.

In an alternative embodiment, the biopsy device 10 permits the outward movement of the biopsy arms 14, operation of the biopsy mechanisms 18, followed by the closing of the biopsy mechanisms 18 and radially inward movement of the biopsy arms 14, in a single action, that is, without retraction of the plunger 22. Such a device could be provided with suitable grooves or openings on the sides of the plunger 22 to permit the biopsy mechanisms 18 and biopsy arms 14 to retract into the sides of the plunger 22 when the plunger 22 has been moved forward a given distance.

Although the invention has been described with reference to a device with biopsy arms 14, the invention is not limited in this regard. The biopsy mechanisms 18 can be provided on other structure or on the housing 12, so long as suitable structure is provided to cause the outward movement of the biopsy mechanisms 18 upon actuation of the device.

The biopsy device 10 according to the invention can be made from any suitable material. Also, the device can be made in a variety of different dimensions and designs without departing from the spirit or essential attributes of the invention. Accordingly, reference should be had to the following claims, rather than to the foregoing specification, as defining the scope of the invention.

We claim:

1. A biopsy device, comprising:
   a housing;
   at least one biopsy mechanism moveably connected to said housing;
   at least one actuator for moving said biopsy mechanism outward relative to said housing and for operating said biopsy mechanism; and
   a plurality of radially spaced biopsy arms spaced about an end of said housing, a first end of each biopsy arm being connected to said housing, a respective biopsy mechanism being provided at an opposing end of each respective biopsy arm.

2. A biopsy device comprising a housing with a moveable actuator and further comprising a plurality of biopsy arms, each having a biopsy mechanism, movement of said actuator moving each of said biopsy arms radially outward relative to said housing and actuating each of said corresponding biopsy arms and biopsy mechanisms to cause said biopsy mechanisms to engage surrounding tissue and remove a biopsy sample.

3. A biopsy device comprising a housing with a moveable actuator and at least one moveable biopsy arm, each said at least one biopsy arm comprising a biopsy mechanism, movement of said actuator moving each said biopsy arm radially outward relative to said housing and operating each said biopsy mechanism to cause each said biopsy mechanism to engage surrounding tissue and remove a biopsy sample;
   wherein each said biopsy mechanism is biased to a closed position; and
   wherein a cam is operatively connected to each said biopsy mechanism, contact between said actuator and said cam causing each said biopsy mechanism to open against said biasing.

4. The biopsy device of claim 3, wherein each said at least one biopsy arm is provided on a head, said head being detachable from said housing.

5. A method of taking a biopsy sample, comprising the steps of:
   providing a plurality of biopsy mechanisms which are moved and operated by operation of an actuator;
   positioning said biopsy mechanisms adjacent to a tissue; and
   manipulating said actuator to cause each said biopsy mechanism to move toward said tissue and to remove a biopsy sample from said tissue.

* * * * *